US012672792B2

(12) United States Patent
Jeon et al.

(10) Patent No.: US 12,672,792 B2
(45) Date of Patent: Jul. 7, 2026

(54) ELECTROMAGNETIC SHAPE SENSOR INTEGRATED WITH WIRE-DRIVEN ROBOT

(71) Applicant: KOREA INSTITUTE OF SCIENCE AND TECHNOLOGY, Seoul (KR)

(72) Inventors: Jiyun Jeon, Seoul (KR); Chunwoo Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 233 days.

(21) Appl. No.: 18/107,277

(22) Filed: Feb. 8, 2023

(65) Prior Publication Data

US 2023/0256628 A1 Aug. 17, 2023

(30) Foreign Application Priority Data

Feb. 11, 2022 (KR) ........................ 10-2022-0018201

(51) Int. Cl.
| | |
|---|---|
| *B25J 19/02* | (2006.01) |
| *A61B 5/06* | (2006.01) |
| *A61B 34/20* | (2016.01) |
| *A61M 25/01* | (2006.01) |
| *B25J 9/16* | (2006.01) |
| *B25J 19/00* | (2006.01) |

(52) U.S. Cl.
CPC .............. *A61B 5/065* (2013.01); *A61B 5/062* (2013.01); *A61B 34/20* (2016.02); *A61M 25/0127* (2013.01); *A61M 25/0147* (2013.01); *A61B 2034/2051* (2016.02); *A61B 2034/2061* (2016.02); *A61M 2025/0166* (2013.01)

(58) Field of Classification Search
CPC .... A61B 2034/2051; A61B 2034/2061; A61B 34/20; A61B 5/062; A61B 5/065; A61M 2025/0166; A61M 25/0127; A61M 25/0147; B25J 13/088; B25J 18/06; B25J 9/104
See application file for complete search history.

(56) References Cited

U.S. PATENT DOCUMENTS

| | | | |
|---|---|---|---|
| 10,226,304 | B2 | 3/2019 | Iordachita et al. |
| 10,568,700 | B2 | 2/2020 | Donhowe et al. |
| 2013/0303945 | A1 | 11/2013 | Blumenkranz et al. |
| 2016/0166341 | A1 | 6/2016 | Iordachita et al. |
| 2020/0085514 | A1 | 3/2020 | Blumenkranz |
| 2020/0146757 | A1 | 5/2020 | Fenech et al. |
| 2020/0275860 | A1 | 9/2020 | Duindam |

FOREIGN PATENT DOCUMENTS

| | | |
|---|---|---|
| KR | 10-1764327 B1 | 8/2017 |

OTHER PUBLICATIONS

Jeon, Jiyun, and Chunwoo Kim. "Shape sensor using magnetic induction with frequency sweeping for medical catheters." 2021 IEEE International Conference on Robotics and Automation (ICRA 2021). IEEE, May 31-Jun. 4, 2021. (pp. 7137-7143).

*Primary Examiner* — Michael T Rozanski
(74) *Attorney, Agent, or Firm* — NSIP Law

(57) ABSTRACT

Provided is an electromagnetic shape sensor integrated with a wire-driven robot. The electromagnetic shape sensor for sensing a shape of the wire-driven robot according to the embodiment includes an excitation coil configured to surround at least a part of an outer peripheral surface of the tube, and a plurality of sensing coils configured to each surround at least a part of an outer peripheral surface of the wire.

3 Claims, 17 Drawing Sheets

ELECTROMAGNETIC SHAPE SENSOR INTEGRATED WITH WIRE-DRIVEN ROBOT

CROSS-REFERENCE TO RELATED APPLICATION

The present application claims priority to Korean Patent Application No. 10-2022-0018201, filed Feb. 11, 2022, the entire contents of which are incorporated herein for all purposes by this reference.

BACKGROUND OF THE INVENTION

Field of the Invention

The present invention relates to an electromagnetic shape sensor, and more particularly, to an electromagnetic shape sensor integrated with a wire-driven robot to utilize an existing structure of a general wire-driven robot.

DESCRIPTION OF NATIONAL SUPPORT RESEARCH AND DEVELOPMENT

This study was conducted with the support from Research and Development (R&D) Fund (Main Business Fund) of the Korea Institute of Science and Technology funded by the Ministry of Science and ICT of Korea, and the project title is [MIDAS Original Technology Development to Lead the Era of Surgery 4.0, Project No. 1711152122, Detailed Project No. 2E31070].

Description of the Related Art

Minimum invasive surgery refers to surgery that is performed while minimizing an incision site without performing laparotomy. The advantage of the minimum invasive surgery is that there is almost no scar or sequelae, little bacterial infection exposure occurs, and fast recovery is enabled because the incision site is small. Because a surgical device in the related art has a hard and fixed structure, there is a problem in that it is difficult to search an interior of a human body without causing wounds in surrounding tissue. In addition, a wire-driven robot has been proposed to overcome the restriction on the surgical device in the related art and is used for the minimum invasive surgery.

It is necessary to detect, in real time, a shape of the invading wire-driven robot during three-dimensional surgery using the wire-driven robot. To this end, shape sensors disclosed in U.S. patent Ser. No. 10/226,304 B2 (Patent Document 1) and U.S. Patent Application Publication No. 2020-0146757 A1 (Patent Document 2) have been proposed.

Patent Document 1 discloses a technology using an optical fiber sensor, particularly, a fiber Bragg grating (FBG) based sensor. The FBG sensor is sensitive to a change in temperature, a large amount of cost is required for an interrogator to measure the FBG sensor, and high precision is required to assemble a sensor fiber to a continuous body robot body in consideration of the alignment of fibers and efficiency in transmitting deformation in a cross-section of a continuous body robot, which causes a problem of very high manufacturing difficulty.

Patent Document 2 discloses a technology using an EM sensor using electromagnetic tracking. Patent Document 2 discloses a configuration in which an external magnetic field generator additionally configured together with a wire-driven robot is used to sense a shape of a wire-driven robot. For this reason, there are problems in that a set-up magnitude of an entire device increases, and the device is affected by noise caused by peripheral metal devices.

SUMMARY OF THE INVENTION

The present invention has been made in an effort to solve the above-mentioned problems, and an object of the present invention is to provide an electromagnetic shape sensor integrated with a wire-driven robot to utilize a structure of the wire-driven robot in the related art.

An exemplary embodiment of the present invention provides an electromagnetic shape sensor, which is configured to sense a shape of a wire-driven robot including a tube extending in one direction, a plurality of wires configured to steer the tube, and a body configured to accommodate the tube and the plurality of wires, the electromagnetic shape sensor including: an excitation coil configured to surround at least a part of an outer peripheral surface of the tube; and a plurality of sensing coils corresponding to the plurality of wires and configured to each surround at least a part of an outer peripheral surface of the corresponding wire.

Another exemplary embodiment of the present invention provides a wire-driven continuous body robot with which an electromagnetic shape sensor is integrated, the wire-driven continuous body robot including: a tube extending in one direction; a plurality of wires configured to steer the tube; a plurality of disks connected to one another in series and connected to be rotatable about a rotation axis, the plurality of disks each including a central opening penetrated by the tube, and a plurality of circumferential openings disposed to have different centers from the central opening, spaced apart from one another in a circumferential direction, and penetrated by the plurality of wires; an excitation coil configured to surround at least a part of an outer peripheral surface of the tube; and a plurality of sensing coils configured to each surround at least a part of an outer peripheral surface of each of the plurality of wires.

The electromagnetic shape sensor integrated with a wire-driven robot according to the embodiment of the present invention uses the magnetic field method, which makes it possible to provide excellent living body compatibility, durability, and heat resistance in virtue of characteristics of the copper coil. In addition, it is possible to use the existing space of the wire-driven robot in the related art without change and easily perform the installation and operation without the necessity of other external devices.

The electromagnetic shape sensor integrated with a wire-driven robot according to the embodiment of the present invention may estimate the shape of the wire-driven robot through the prediction model configured to estimate the rotation angle and the bending angle of the wire-driven robot on the basis of the difference in voltage between the sensing coils symmetrically disposed. Therefore, it is possible to provide the more accurate results and implement robustness by using the difference in induced voltage between the sensing coils 110 even though disturbing metal is present inside or outside of the electromagnetic shape sensor.

The effects obtained by the present invention are not limited to the aforementioned effects, and other effects, which are not mentioned above, will be clearly understood by those skilled in the art from the following description.

DETAILED DESCRIPTION OF THE INVENTION

Figure 1:
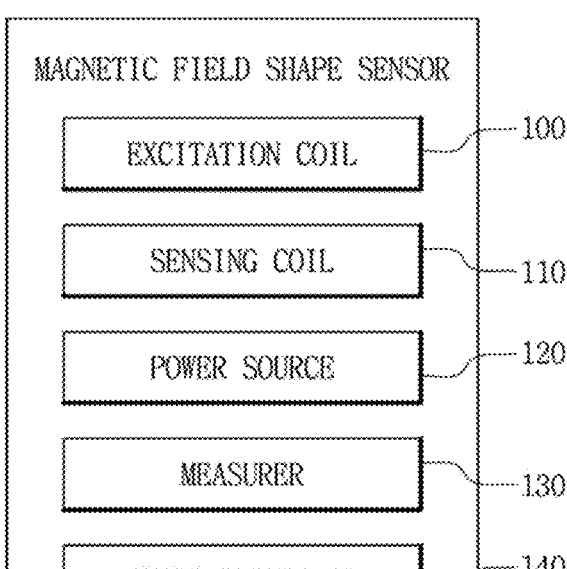
FIG. 1 is a block diagram illustrating a configuration of an electromagnetic shape sensor according to an embodiment of the present invention.

Hereinafter, embodiments of the present invention will be described in detail with reference to the accompanying drawings. The present invention will be described with reference to the embodiment illustrated in the drawings, but the description of the present invention is made as one embodiment. The technical spirit and the key components and operations of the present invention are not limited by the embodiment.

FIG. 1 is a block diagram illustrating a configuration of an electromagnetic shape sensor according to an embodiment of the present invention.

Referring to FIG. 1, an electromagnetic shape sensor 10 according to the embodiment of the present invention includes an excitation coil 100, a plurality of sensing coils 110, a power source 120, a measurer 130, and a shape predictor 140.

The excitation coil 100 may generate a magnetic field in response to applied power. The sensing coil 110 may generate induced voltage in response to the magnetic field applied to the excitation coil 100. The power source 120 is configured to supply power to the excitation coil 100 and sense the induced voltage of the sensing coil 110. In addition, on the basis of the sensed induced voltage, the shape predictor 140 predicts a shape of a device to which the electromagnetic shape sensor 10 is applied. The electromagnetic shape sensor 10 according to the embodiment of the present invention may be a sensor configured to sense a shape of a wire-driven robot. The shape predictor 140 may be configured to predict the shape of the wire-driven robot.

Figure 2:
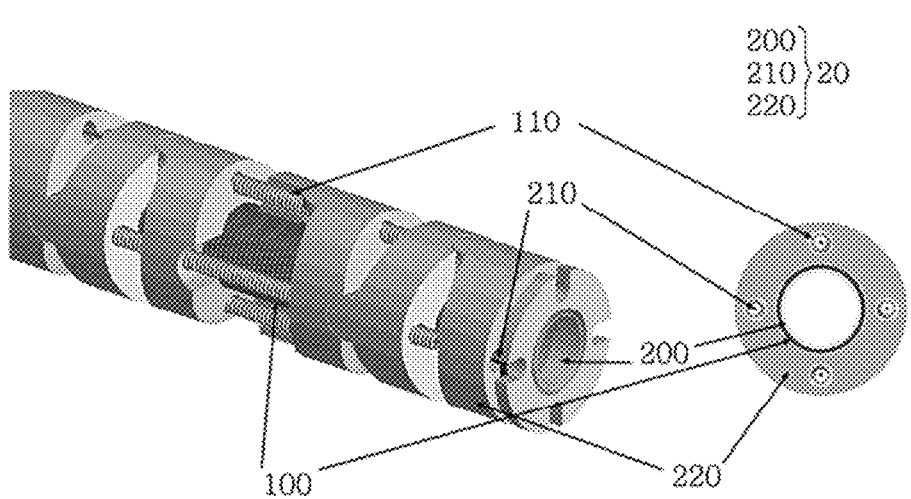
FIG. 2 is a perspective view illustrating a state in which the electromagnetic shape sensor according to the embodiment of the present invention is integrated with a wire-driven robot.
Figure 3:
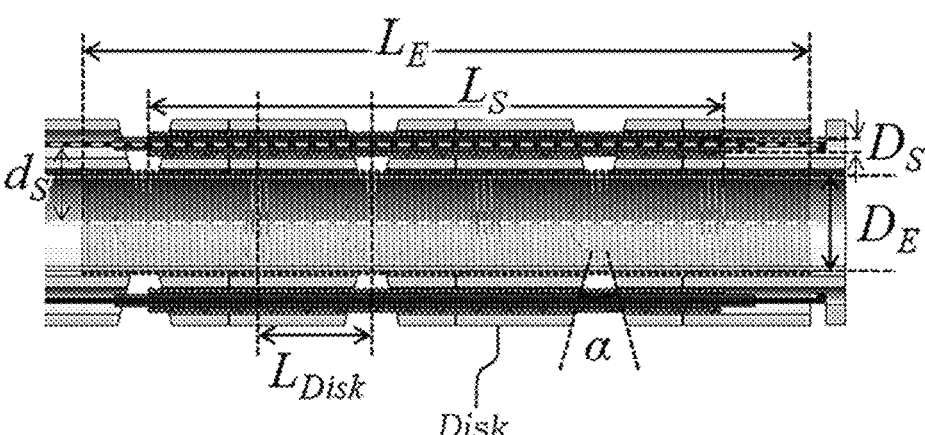
FIG. 3 is a cross-sectional view illustrating a state in which the electromagnetic shape sensor is integrated with the wire-driven robot.

FIG. 2 is a perspective view illustrating a state in which the electromagnetic shape sensor according to the embodiment of the present invention is integrated with a wire-driven robot. FIG. 3 is a cross-sectional view illustrating a state in which the electromagnetic shape sensor is integrated with the wire-driven robot.

Referring to FIGS. 2 and 3, the wire-driven robot 20 includes a tube 200 extending in one direction, a plurality of wires 210 configured to steer the tube, and a body 220 configured to accommodate the tube and the plurality of wires.

The tube 200 may be made of a flexible material and bent by a tensile force of the wires. For example, the tube 200 may be, but not limited to, a silicone tube. The plurality of wires 210 may be configured to steer the tube 200. The plurality of wires 210 may be symmetrically disposed with respect to the tube 200. For example, as illustrated in FIG. 2, four wires 210 may be provided and disposed in upward, downward, leftward, and rightward directions with respect to the tube 200. That is, the four wires may include two wires symmetrically disposed with respect to an X-axis on an X-Y plane, which is defined such that a center of a cross-section of the tube 200 is an origin of the X-Y plane, and two wires symmetrically disposed with respect to a Y-axis on the X-Y plane. Each of the plurality of wires 210 may be, but not limited to, a nitinol wire.

The body 220 is configured to accommodate the tube 200 and the wires 210. The wire 210 may be disposed in the body 220. In a state in which one end of the wire 210 is fixed, the other end of the wire 210 may be coupled to a device, such as a pulley, configured to adjust a length of the wire. Therefore, the length of the wire 210 may be adjusted. That is, the wire 210 may serve as a tendon. The tube 200 may be bent by a change in length of the wire 210, such that an overall shape of the wire-driven robot 20 may be changed.

The body 220 includes a plurality of disks connected in series and configured to be rotatable about a rotation axis. Referring to FIG. 3, it can be seen that the plurality of disks is connected continuously through a rotary joint so as to be rotatable from −α to α. L$_{Disk}$ in FIG. 3 means a length of one disk. In addition, the plurality of disks may be rotated in two directions by joints having perpendicular axes and disposed alternately. In addition, the plurality of disks may each include a central opening penetrated by the tube 200, and a plurality of circumferential openings having different centers from the central opening, spaced apart from one another in a circumferential direction, and penetrated by the plurality of wires 210. That is, the tube 200 extends while passing through the central openings of the plurality of disks. The plurality of wires 210 may extend while passing through the corresponding circumferential openings of the disks.

In this case, the electromagnetic shape sensor 10 may be integrated with the wire-driven robot 20. The electromagnetic shape sensor 10 may be disposed on the entire wire-driven robot 20, but the present invention is not limited thereto. The electromagnetic shape sensor 10 may be disposed partially at a position and region of the wire-driven robot 20 where the shape of the wire-driven robot 20 is required to be measured.

Specifically, the excitation coil 100 may be configured to surround at least a part of the outer peripheral surface of the tube 200. The excitation coil 100 may extend in an extension direction of the tube 200 while surrounding at least a part of the outer peripheral surface of the tube 200. The plurality of sensing coils 110 corresponds to the plurality of wires 210.

Each of the sensing coils 110 may surround at least a part of an outer peripheral surface of the corresponding wire 210. Each of the sensing coils 110 may extend in an extension direction of the wire 210 while surrounding at least a part of the outer peripheral surface of the corresponding wire 210. The plurality of sensing coils 110 may be symmetrically positioned with respect to the excitation coil 100. In this case, when the four wires 210 are provided to correspond to the four directions, the sensing coils 110 may also be provided to correspond to the four wires 210. As illustrated in FIG. 2, the sensing coils 110 may be disposed in the upward, downward, leftward, and rightward directions with respect to the excitation coil 100.

In FIG. 3, $L_E$ and $D_E$ respectively mean a length and a diameter of the excitation coil 100, and $L_s$ and $D_s$ respectively mean a length and a diameter of the sensing coil 110. As illustrated in FIG. 3, the sensing coil 110 and the excitation coil 100 may be designed to correspond to the structure of the wire-driven robot 20 in the related art and use the space in the related art without change. That is, the installation and operation of the wire-driven robot 20 may be easily performed without the necessity of other external devices.

Figure 4A:
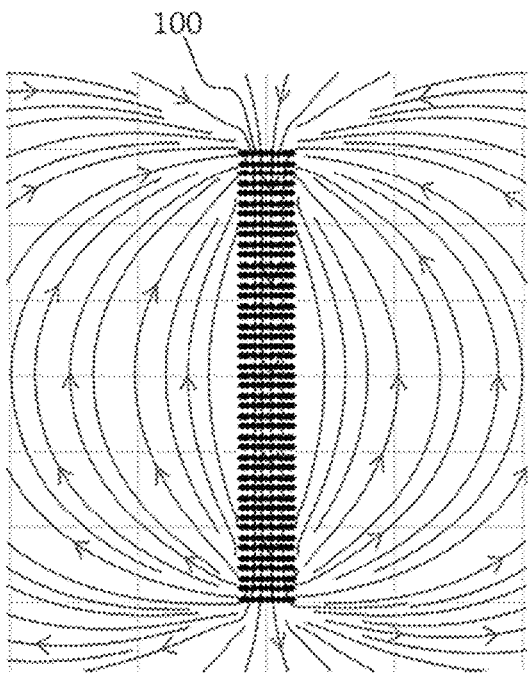
FIGS. 4A and 4B are views exemplarily illustrating a magnetic field generated by an excitation coil that varies by being bent.
Figure 4B:
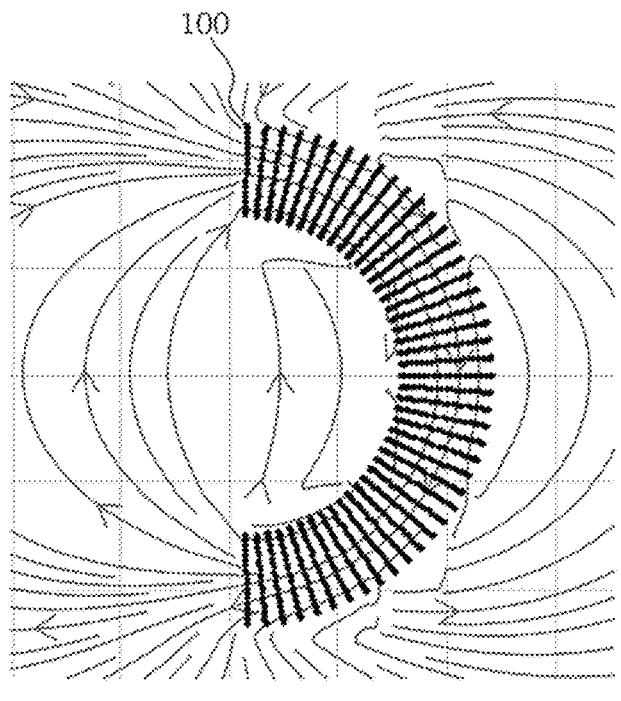

FIGS. 4A and 4B are views exemplarily illustrating a magnetic field generated by the excitation coil that varies by being bent.

In a state in which the tube 200 is not bent, a magnetic field is generated by the excitation coil 100 is shown as FIG. 4A. That is, the magnetic field is symmetrically formed with respect to the excitation coil 100, and there is no substantial difference between induced voltages applied to the sensing coils 110 disposed symmetrically with respect to the excitation coil 100. However, when the tube 200 is bent by adjusting the length of the wire 210, all the excitation coil 100 and the sensing coils 110 are bent, such that the magnetic field generated by the excitation coil 100 also changes, as illustrated in FIG. 4B. Depending on the change in magnetic field, there occurs a difference between the induced voltages applied to the sensing coils 110 disposed symmetrically with respect to the excitation coil 100.

The measurer 130 may measure the induced voltage measured by the sensing coils 110 disposed symmetrically with respect to the excitation coil 100. The measurer 130 may be configured to measure the voltages of the plurality of sensing coils 110 and provide the measured to the shape predictor 140.

The shape predictor 140 may be configured to predict the shape of the wire-driven robot 20 on the basis of the induced voltage provided from the power source 120. Specifically, the plurality of sensing coils 110 may include the sensing coils disposed symmetrically with respect to the X-axis on the X-Y plane, which is defined such that the center of the cross-section of the tube 200 is defined as the origin of the X-Y plane, and the sensing coils disposed symmetrically with respect to the Y-axis on the X-Y plane. When the four sensing coils 110 are provided, the two sensing coils may be disposed symmetrically with respect to the X-axis, and the remaining two sensing coils may be disposed symmetrically with respect to the Y-axis. The shape predictor 140 may predict the shape of the wire-driven robot 20 on the basis of a difference ($Sig_x$) in induced voltage between the sensing coils disposed symmetrically with respect to the X-axis and a difference ($Sig_y$) in voltage between the sensing coils disposed symmetrically with respect to the Y-axis. That is, the shape of the wire-driven robot 20 is estimated by using a difference value between the symmetrically disposed sensing coils instead of using a simply measured induced voltage. Therefore, it is possible to prevent the occurrence of error in a situation in which the induced voltage is changed by an external magnetic field.

Specifically, the shape predictor 140 may include a first prediction model configured to predict a rotation angle $\varphi$ and a bending angle $\theta$ of the wire-driven robot 20 on the basis of the difference ($Sig_x$) in induced voltage between the sensing coil disposed symmetrically with respect to the X-axis, and a second prediction model configured to predict a rotation angle $\varphi$ and a bending angle $\theta$ of the wire-driven robot 20 on the basis of a difference ($Sig_y$) in induced voltage between the sensing coils disposed symmetrically with respect to the Y-axis. The first prediction model may be a prediction model established in advance on the basis of experimentally measured data sets (input data: $Sig_x$, output data: rotation angle $\varphi$ and bending angle $\theta$). The second prediction model may be a prediction model established in advance on the basis of experimentally measured data sets (input data: $Sig_y$, output data: rotation angle $\varphi$ and bending angle $\theta$). Each of the first and second prediction models may be established through at least one analysis model among a linear regression model, a logistic regression model, a machine learning model, and a neural network model.

The shape predictor 140 may create prediction shape information used to predict the shape of the wire-driven robot 20 in consideration of the predicted rotation angle $\varphi$, the predicted bending angle $\theta$, and basic information (an overall length, a diameter, etc.) of the wire-driven robot 20.

Embodiment

The electromagnetic shape sensor 10 and the wire-driven robot 20 were configured on the basis of a condition as shown in Table 1. The wire-driven robot 20 was configured as a continuous body drive robot in which disks were connected in series as illustrated in FIGS. 2 and 3.

TABLE 1

| Diameter of excitation coil, $D_E$ (mm) | 4 | Diameter of sensing coil, $D_S$ (mm) | 1 |
|---|---|---|---|
| Length of excitation coil, $L_E$ (mm) | 30 | Length of sensing coil, $L_S$ (mm) | 20 |
| Rotation angle of disk, $\alpha$ (deg) | 30 | Length of disk, $L_{Disk}$ (mm) | 4.36 |

Figure 5:
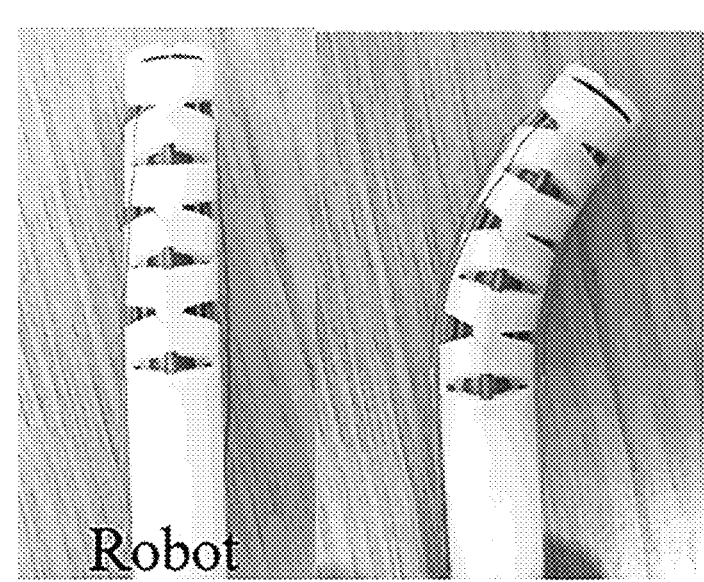
FIG. 5 is a view illustrating an actual image of the wire-driven robot with which the electromagnetic shape sensor configured according to the embodiment is integrated.

FIG. 5 is a view illustrating an actual image of the wire-driven robot 20 with which the electromagnetic shape sensor 10 configured according to the embodiment is integrated. Referring to FIG. 5, it can be seen that the entire wire-driven robot 20 is bent by manipulating the wires. In addition, the power source 120 of the electromagnetic shape sensor 10 is configured to be excited at a frequency of 800 kHz by a function generator (WF1974, NF Inc., Japan). The measurer 130 is configured as an oscilloscope (MD032, Tektronix, USA) and measures the induced voltage of the sensing coils 110. The sensing coil 110 and the excitation coil 100 were each configured as a copper coil. In addition, the shape predictor 140 was configured to include the first and second prediction models learned by a multivariate linear regression model so as to predict the rotation angle $\varphi$ and the bending angle $\theta$ of the wire-driven robot 20 on the basis of the inputted $Sig_x$ and $Sig_y$.

Experimental Example 1

An experiment was performed to check the performance of the electromagnetic shape sensor 10 integrated with the wire-driven robot 20 configured according to the embodi-ment, specifically, the performance of the first and second prediction models.

The first and second prediction models were established through the multivariate linear regression model so as to predict the rotation angle φ and the bending angle θ of the wire-driven robot 20 on the basis of the inputted Sig$_x$ and Sig$_y$.

Figure 6A:
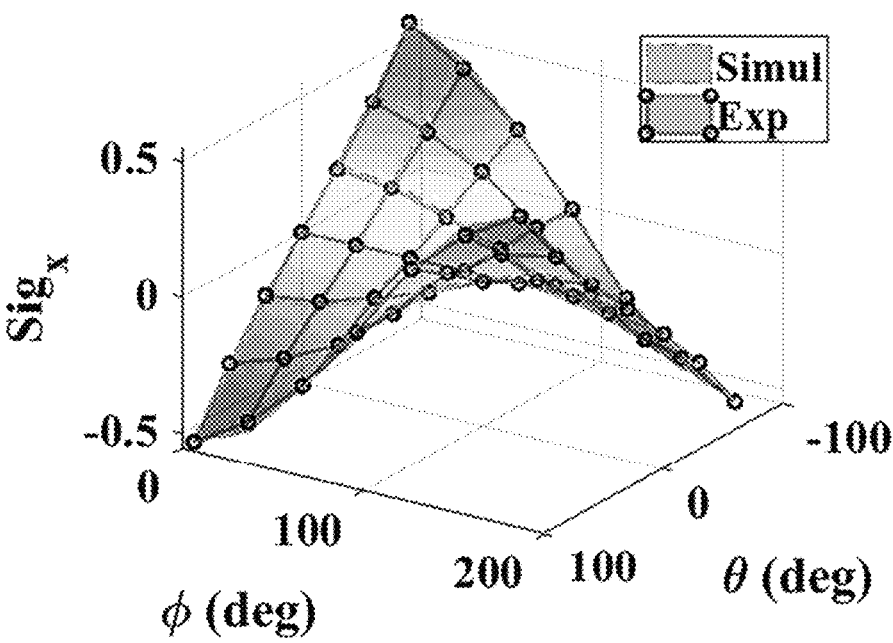
FIG. 6A is a three-dimensional graph for comparing a first prediction model (Simul) and an experimental result (Exp)

FIG. 6A is a three-dimensional graph for comparing the first prediction model (Simul) and an experimental result (Exp). That is, FIG. 6A is a three-dimensional graph for comparing the rotation angle φ and the bending angle θ, which are predicted by the first prediction model (Simul) corresponding to inputted Sig$_x$, with a result of performing the experiment (Exp) for measuring Sig$_x$ after bending the wire-driven robot 20 by the particular rotation angle φ and the particular bending angle θ. Referring to FIG. 6A, it can be seen that the rotation angle φ and the bending angle θ, which are predicted according to the inputted Sig$_x$, are similar to the results which are experimentally checked actually.

Figure 6B:
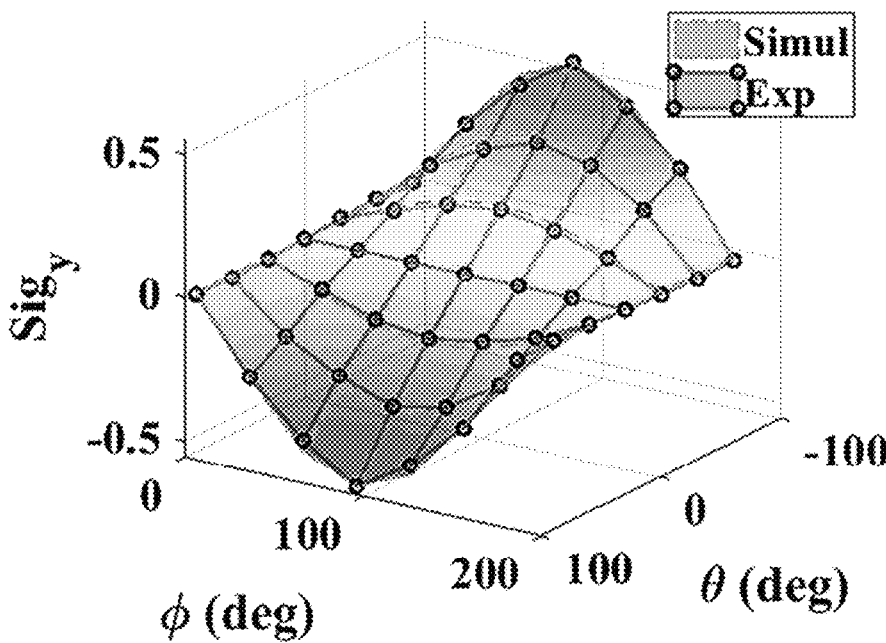
FIG. 6B is a three-dimensional graph for comparing a second prediction model (Simul) and the experimental result (Exp).

In addition, FIG. 6B is a three-dimensional graph for comparing the second prediction model (Simul) and the experimental result (Exp). That is, FIG. 6B is a three-dimensional graph for comparing the rotation angle φ and the bending angle θ, which are predicted by the second prediction model (Simul) corresponding to inputted Sig$_y$, with a result of performing the experiment (Exp) for mea-suring Sig$_y$ after bending the wire-driven robot 20 by the particular rotation angle φ and the particular bending angle θ. Referring to FIG. 6B, it can be seen that the rotation angle φ and the bending angle θ, which are predicted according to the inputted Sig$_y$, are similar to the results which are experimentally checked actually.

Experimental Example 2

An experiment was performed to check the performance of the electromagnetic shape sensor 10 integrated with the wire-driven robot 20 configured according to the embodi-ment, specifically, the performance of the electromagnetic shape sensor 10 for predicting the shape.

Figure 7:
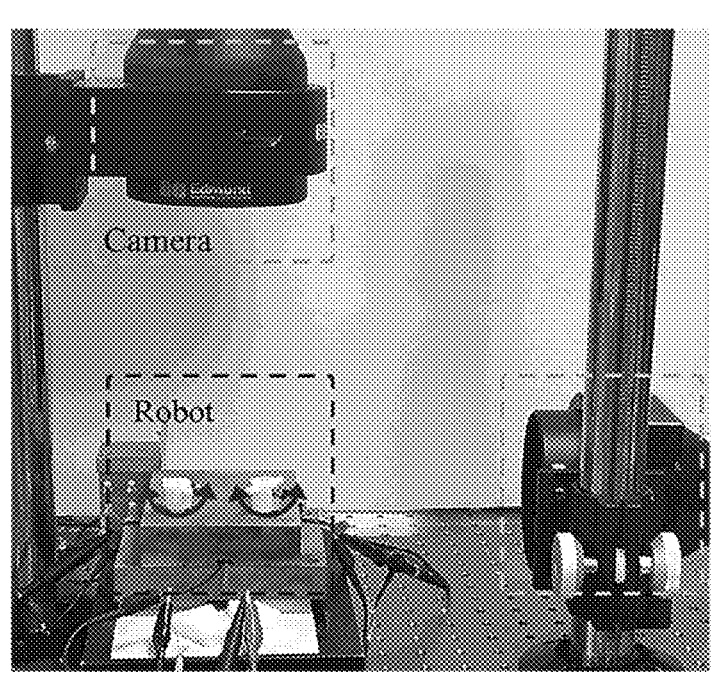
FIG. 7 is a view illustrating an experimental device for performing a shape prediction performance experiment.
Figure 8:
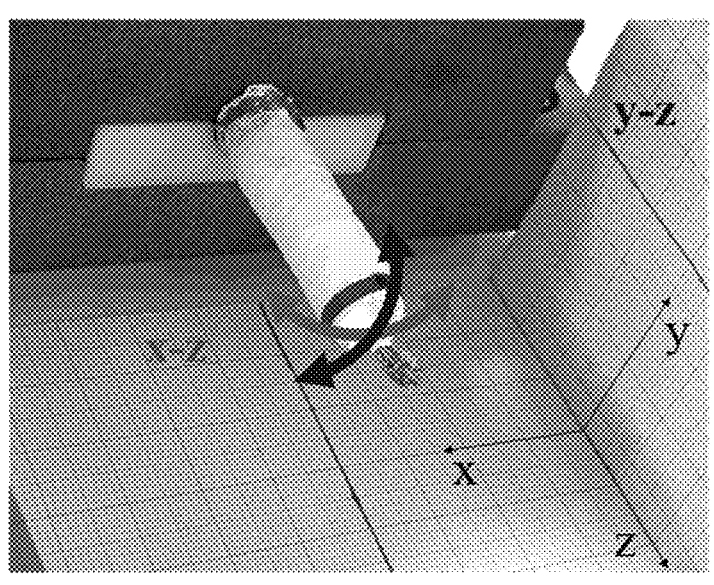
FIG. 8 is a view illustrating the wire-driven robot configured to be manipulated by a manipulator.
Figure 9A:
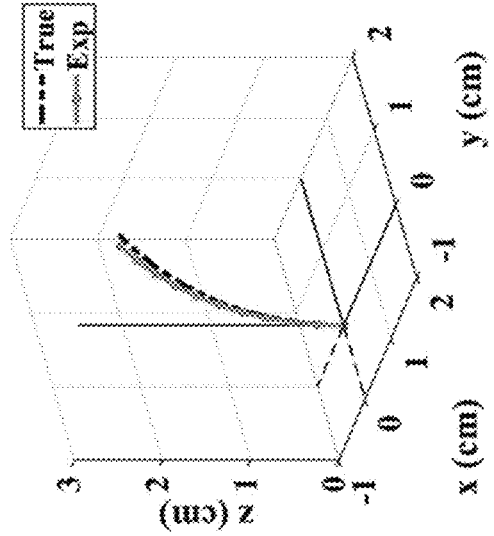
FIGS. 9A to 9D are views illustrating images of the moved wire-driven robot and graphs for comparing actually measured values (True) of the moved wire-driven robot and prediction shape information (Exp) predicted by the electromagnetic shape sensor.
Figure 9A:
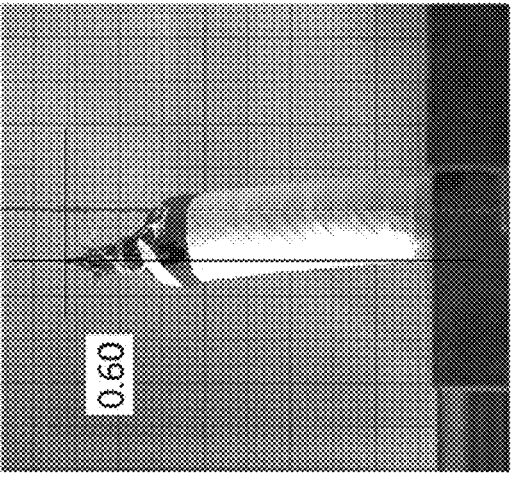
Figure 9A:
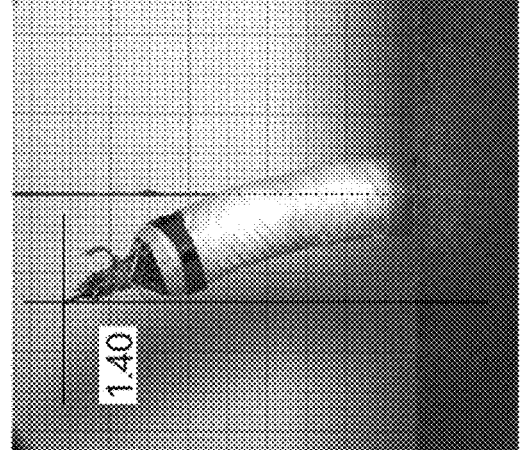
Figure 9B:
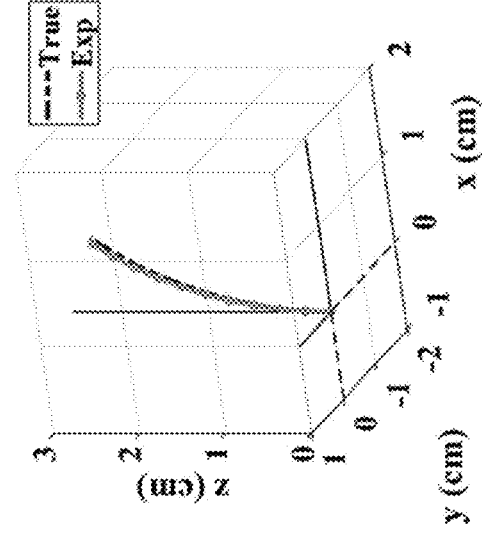
Figure 9B:
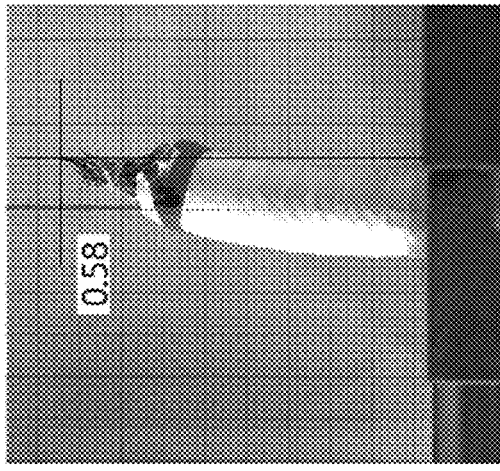
Figure 9B:
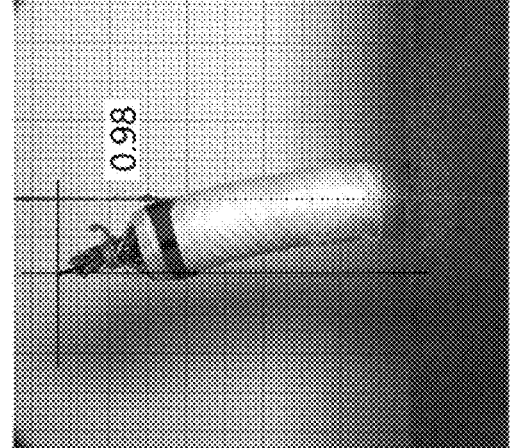
Figure 9C:
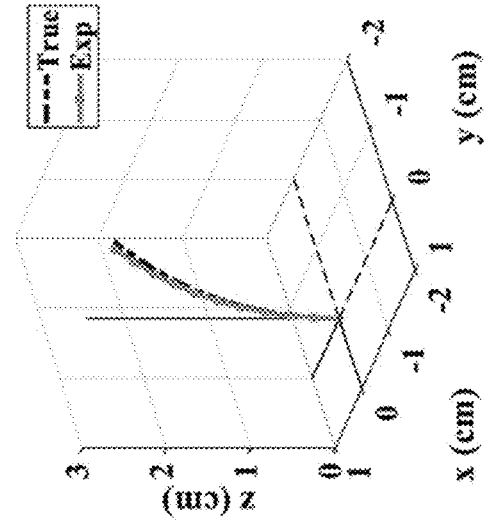
Figure 9C:
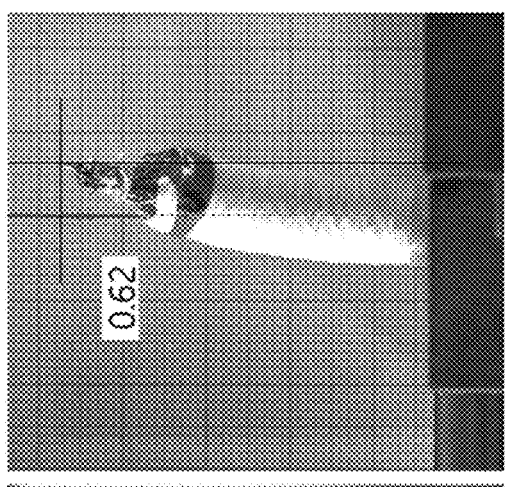
Figure 9C:
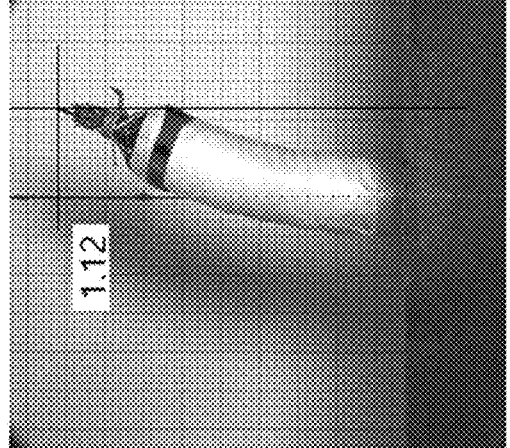
Figure 9D:
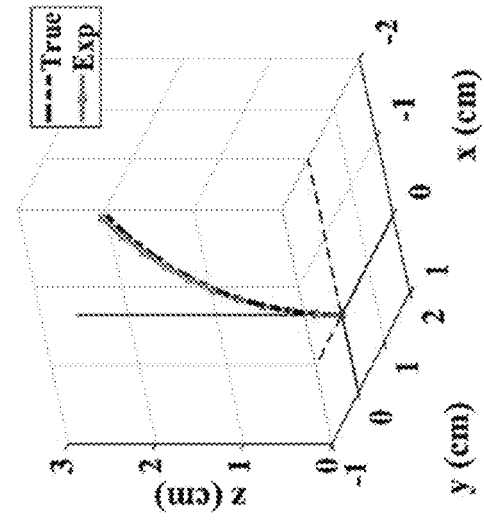
Figure 9D:
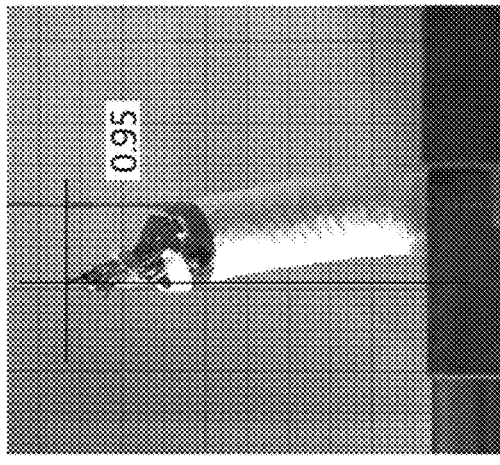
Figure 9D:
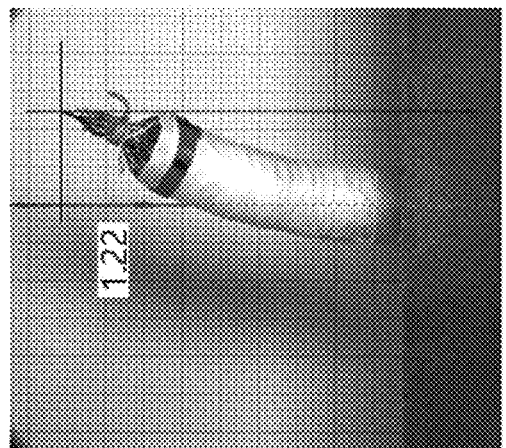

FIG. 7 is a view illustrating an experimental device for performing a shape prediction performance experiment. The experimental device includes a camera configured to capture an image of a shape of the wire-driven robot 20, a reference point, and a manipulator configured to bend the wire-driven robot 20. FIG. 8 is a view illustrating the wire-driven robot configured to be manipulated by the manipulator. The posi-tions of the wire-driven robot on the X-Z plane and the Y-Z plane may be changed by the manipulator. The camera captured images of the wire-driven robot moved on the X-Z plane and the Y-Z plane and measured degrees of move-ments relative to the reference point. In addition, prediction shape information was created by predicting the shape of the moved wire-driven robot by using the electromagnetic shape sensor 10.

FIGS. 9A to 9D are views illustrating images of the moved wire-driven robot on the X-Z plane and the Y-Z plane and graphs for comparing actually measured values (True) of the moved wire-driven robot and prediction shape infor-mation (Exp) predicted by the electromagnetic shape sensor 10. Actually, measured values (True), which were measured by the camera by adjusting the positions of the wire-driven robot four times, were compared with prediction shape information (Exp) predicted by the electromagnetic shape sensor 10. Referring to FIGS. 9A to 9D, it can be seen that even though some errors occurred, the results predicted by the electromagnetic shape sensor according to the present embodiment are similar to the measured values according to the actual movements.

Experimental Example 3

An experiment was performed to check that the electro-magnetic shape sensor 10 integrated with the wire-driven robot 20 configured according to the embodiment has dura-bility against disturbance of the magnetic field.

The surgery using the wire-driven robot 20 uses various metallic tools such as cutter, forceps, pincers, and wires inside and outside the robot. When a conductive metal object is present in a magnetic field that varies over time, the disturbance of the magnetic field may occur. Therefore, it is necessary to evaluate firmness and robustness of the pro-posed sensor against disturbance of electromagnetic waves caused by the metal object.

First, an experiment was performed on the disturbance of the magnetic field that occurred when nitinol and steel passed through the interior of the robot. In the experimental example, a steel wire and a nitinol wire, which each had a diameter of 0.5 mm, were inserted into the tube through the central opening through 7 divided steps, and Sig$_x$, which was the difference in induced voltage between the sensing coil changing depending on and corresponding to the induced voltage, was measured in each step. For example, in step 1, the disturbing metal is present outside the tube. In step 2, the disturbing metal is present at the end of the excitation coil. In next step, the disturbing metal is inserted by ¼ of the length of the excitation coil. Then, in step 6, the disturbing metal is completely inserted into the excitation coil. In step 7, the disturbing metal passes through the tube.

Figure 10A:
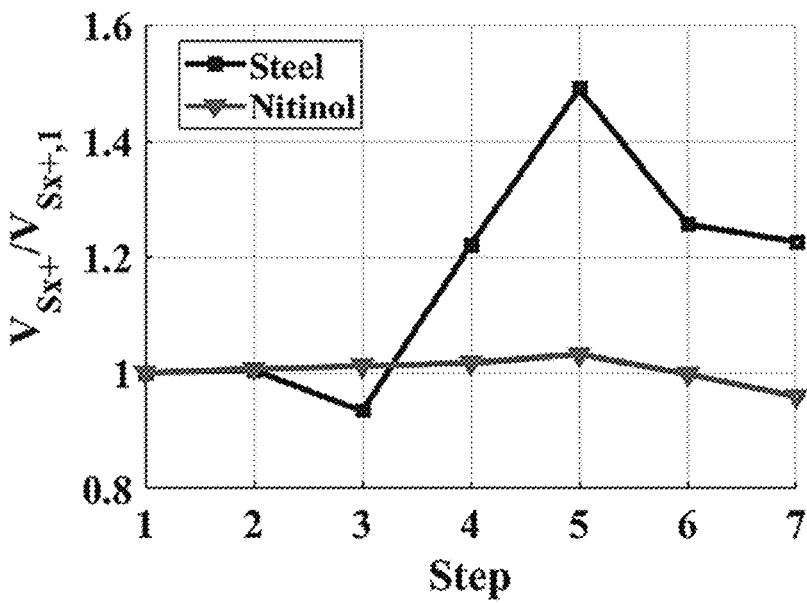
FIG. 10A is a graph showing a change in induced voltage (θ=0 deg) of a sensing coils 110 caused by disturbing metal inserted according to step 7.

FIG. 10A is a graph showing a change in induced voltage (θ=0 deg) of the sensing coils 110 caused by disturbing metal inserted according to step 7. The result was normal-ized as voltage in step in order to estimate the relative change. It can be seen that as the steel is inserted into the excitation coil in steps 3 to 5, the sensing coils 110 voltage induced is changed since the steel acts as a magnetic force source. It can be seen that after the steel is completely inserted, the magnetic fields of the excitation coil and the sensing coils 110 are constantly maintained and there is almost no change in voltage in steps 6 and 7. It can be seen that the induced sensor voltage is constantly maintained regardless of the degree of insertion of the nitinol.

Figure 10B:
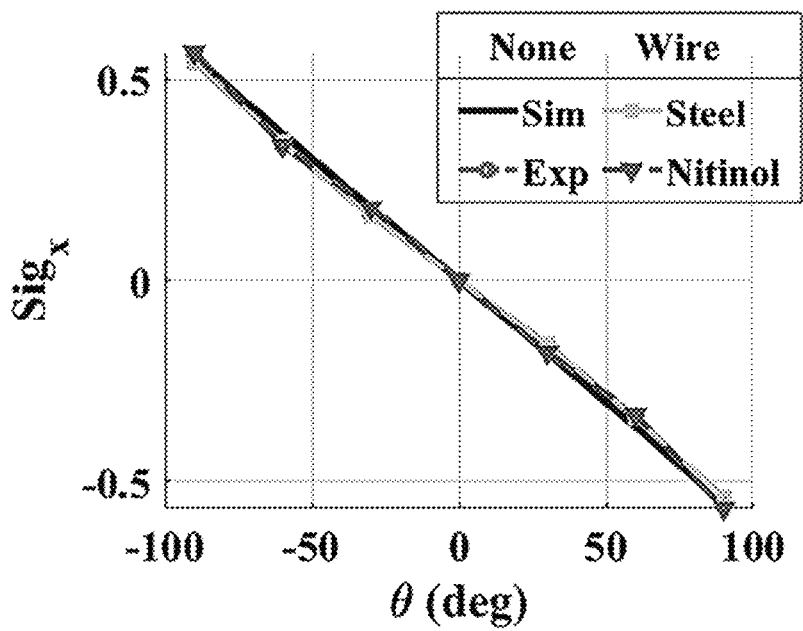
FIG. 10B is a graph showing a change in Sig$_x$ measured in step 4 while changing θ (−90:30:90) deg at φ=0 deg.
Figure 10C:
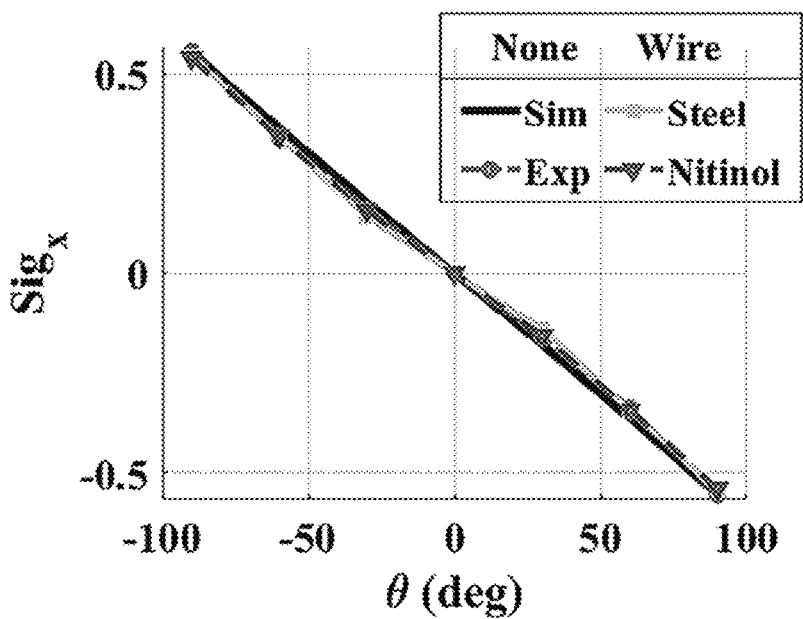
FIG. 10C is a graph showing a change in Sig$_x$ measured in step 7 while changing θ (−90:30:90) deg at φ=0 deg.

FIG. 10B is a graph showing a change in Sig$_x$ measured in step 4 while changing θ (−90:30:90) deg at φ=0 deg. FIG. 10C is a graph showing a change in Sig$_x$ measured in step 7 while changing θ (−90:30:90) deg at φ=0 deg. Referring to FIGS. 10B and 10C, it can be seen that the result of Sig$_x$ according to the insertion of steel and the result of Sig$_x$ according to the insertion of nitinol are similar regardless of steps. That is, even though the induced voltage of the sensing coils 110 may be changed by the insertion of the disturbing metal such as steel, the tendency of Sig$_x$ is maintained because the differences between the sensing coils 110 are offset. It can be ascertained that the sensor according to the present embodiment, which is configured to predict the shape by using the difference in induced voltage between the sensing coils 110, has robustness even though the disturbing metal is positioned inside or outside the sensor.

The electromagnetic shape sensor integrated with a wire-driven robot according to the embodiment of the present invention uses the magnetic field method, which makes it possible to provide excellent living body compatibility, durability, and heat resistance in virtue of characteristics of the copper coil. In addition, it is possible to use the existing space of the wire-driven robot in the related art without change and easily perform the installation and operation without the necessity of other external devices.

The electromagnetic shape sensor integrated with a wire-driven robot according to the embodiment of the present invention may estimate the shape of the wire-driven robot through the prediction model configured to estimate the rotation angle and the bending angle of the wire-driven robot on the basis of the difference in voltage between the sensing coils symmetrically disposed. Therefore, it is possible to provide the more accurate results and implement robustness by using the difference in induced voltage between the sensing coils 110 even though disturbing metal passes through the electromagnetic shape sensor.

Another exemplary embodiment of the present invention provides a wire-driven robot with which an electromagnetic shape sensor is integrated, the wire-driven robot including: a tube extending in one direction; a plurality of wires configured to steer the tube; a plurality of disks connected to one another in series and connected to be rotatable about a rotation axis, the plurality of disks each including a central opening penetrated by the tube, and a plurality of circumferential openings disposed to have different centers from the central opening, spaced apart from one another in a circumferential direction, and penetrated by the plurality of wires; an excitation coil configured to surround at least a part of an outer peripheral surface of the tube; and a plurality of sensing coils configured to each surround at least a part of an outer peripheral surface of each of the plurality of wires.

In the above-mentioned specific embodiments, the components included in the invention have been expressed as singular or plural components depending on the proposed specific embodiments. However, the singular or plural expression is appropriately selected for the situation proposed for the convenience of description, and the above-mentioned embodiments are not limited by the singular or plural expression. Therefore, the component expressed with a plural term may be configured in a singular form, or the component expressed with a singular term may be configured in a plural form.

While the specific embodiments according to the present invention have been described above, various modifications may be made without departing from the scope of the present invention contained in the various embodiments. Therefore, the scope of the present invention should not be limited to the described exemplary embodiments, and should be defined by not only the claims to be described below, but also those equivalent to the claims.

What is claimed is:

1. A wire-driven continuous body robot with which a magnetic field shape sensor is integrated, the wire-driven continuous body robot comprising:
   a tube extending in one direction;
   a plurality of wires configured to steer the tube; and
   a body comprising a plurality of disks connected to one another in series and connected to be rotatable in two directions by joints having perpendicular axes and disposed alternately and the plurality of disks each includes a central opening penetrated by the tube, and a plurality of circumferential openings having different centers from the central opening, spaced apart from one another in a circumferential direction, and penetrated by the plurality of wires,
   wherein the magnetic field shape sensor comprises:
      an excitation coil configured to entirely and directly surround an outer peripheral surface of the tube; and
      a plurality of sensing coils corresponding to the plurality of wires and configured to each entirely and directly surround an outer peripheral surface of the corresponding wire.

2. The wire-driven continuous body robot of claim 1, wherein the plurality of wires is provided as four wires, two wires of the four wires are disposed symmetrically with respect to an X-axis on an X-Y plane defined such that a center of a cross-section of the tube is an origin of the X-Y plane, and remaining two wires are disposed symmetrically with respect to a Y-axis on the X-Y plane.

3. The wire-driven continuous body robot of claim 1, wherein the excitation coil and the plurality of sensing coils are bent in a direction corresponding to a direction in which the wire-driven continuous body robot is bent, and
   wherein the magnetic field shape sensor further comprises:
      a power source configured to supply power to the excitation coil;
      a measurer configured to measure an induced voltage according to the bending of the plurality of sensing coils, wherein the plurality of sensing coils is provided as four sensing coils, two sensing coils are disposed symmetrically with respect to an X-axis on an X-Y plane defined such that a center of a cross-section of the tube is an origin of the X-Y plane, and the remaining two sensing coils are disposed symmetrically with respect to a Y-axis on the X-Y plane; and
   wherein the robot is configured to determine a rotation angle φ and a bending angle θ of the wire-driven continuous body robot on the basis of a difference ($Sig_x$) in induced voltage between the sensing coils disposed symmetrically with respect to the X-axis by using a first prediction model,
   wherein the first prediction model is a multivariate linear regression model trained to predict the rotation angle φ and the bending angle θ of the wire-driven continuous body robot based on the difference ($Sig_x$),
   wherein the robot is configured to determine rotation angle φ and a bending angle θ of the wire-driven continuous body robot on the basis of a difference ($Sig_y$) in induced voltage between the sensing coils disposed symmetrically with respect to the Y-axis by using a second prediction model, and
   wherein the second prediction model is a multivariate linear regression model trained to predict the rotation angle φ and the bending angle θ of the wire-driven continuous body robot based on the difference ($Sig_y$).

* * * * *